United States Patent
Zhang et al.

(10) Patent No.: US 6,887,981 B2
(45) Date of Patent: May 3, 2005

(54) NATURAL ANTIBACTERIAL PEPTIDE, THE NUCLEOTIDE SEQUENCE ENCODING IT AND THE USE THEREOF

(75) Inventors: Yonglian Zhang, Shanghai (CN); Hsiaochang Chan, Hong Kong (CN); Peng Li, Shanghai (CN); Bin He, Shanghai (CN); Siucheung So, Hong Kong (CN); Yiuwa Chung, Hong Kong (CN); Quan Shang, Shanghai (CN); Youduan Zhang, Shanghai (CN)

(73) Assignee: Shanghai CAS Shenglonda Biotech (Group) Co., Ltd., Shanghai (CN)

( * ) Notice: Subject to any disclaimer, the term of this patent is extended or adjusted under 35 U.S.C. 154(b) by 0 days.

(21) Appl. No.: 10/623,629

(22) Filed: Jul. 21, 2003

(65) Prior Publication Data

US 2004/0058371 A1 Mar. 25, 2004

Related U.S. Application Data

(63) Continuation of application No. PCT/CN02/00032, filed on Jan. 21, 2002.

(30) Foreign Application Priority Data

Jan. 22, 2002 (CN) ........................................ 01105283 A

(51) Int. Cl.[7] .......................... C07K 1/00; C07K 14/00; C07K 17/00
(52) U.S. Cl. ..................................................... 530/350

(58) Field of Search ........................... 530/350; 514/12; 435/7, 6.1; 536/23.1

(56) References Cited

U.S. PATENT DOCUMENTS

| | | |
|---|---|---|
| 5,646,014 A | 7/1997 | Hara |
| 5,707,855 A | 1/1998 | Hancock et al. |
| 5,734,015 A | 3/1998 | Shinnar et al. |
| 6,071,879 A | 6/2000 | Pereira |

FOREIGN PATENT DOCUMENTS

| | | |
|---|---|---|
| JP | 2000-245483 | 2/2000 |

OTHER PUBLICATIONS

Li et al., NCBI Sequence Submissions, AF217089 and AAL55637.*

* cited by examiner

Primary Examiner—Robert A. Wax
Assistant Examiner—Robert B. Mondesi
(74) Attorney, Agent, or Firm—Dorsey & Whitney LLP

(57) ABSTRACT

The invention provides a novel Bin1b protein, and its encoding polynucleotide. Bin1b protein is a natural antimicrobial peptide and associates to sperm maturation. The invention also discloses the preparation and uses of Bin1b protein and nucleic acid. Bin1b protein is useful to treat various diseases, e.g, urogenital infection. The invention also provides a pharmaceutical composition containing Bin1b protein.

5 Claims, 7 Drawing Sheets

FIG. 1

```
   1 GACACCCAGTCATCAGTCACATCTGCTTTCCTGCACAGAGAGAGCGCCATAAAACATGAAGGTTTTGTTACTCTTTGCTGTTTTCTTCTGCTTGGTCCA
                                                                   M  K  V  L  L  L  F  A  V  F  F  C  L  V  Q
 100 AAGAAACTCAG
      R  N  S
                gtaaatgtcttctgagtagccctggagaaggcaggatgccctttaggtttgtagaccacattgaggtgtgtccaggtatcaacattgg
 200 gcacagatggtgggccactctggggctcagggtcggaccacttcctaacgaagaggttttattttgattttttttttgttgttcatttgtcaagagttg
 300 caaattttacagcacggagacacagaggcctatattctccattgtgaataagaaggtctgattgtaacttgagagtttattcaggacagaattacagccg
 400 tacctgtgtcaaaagtgtaattttactgcctcgctgtgagcagagaaggtgttcacatttatgcccctccctacccattacatccacagaacaccagat
 500 gtatgctttaaatgaattttcaaatgagagaaaaataggttcctttaagaaagctagagtccaggtcctgaagccttgaattgctggcagttctgtcaag
 600 gtggactacacccacatctccatgaaccttcccaaccatggtaaaccggatgaacacagtatcacaaatcagtccccagctgaagtccggctattgcagg
 700 agaccagtttcctaaatgttacaggcataggttgggccgctgttgcttttaaacacagggtgtgcaacattgttaaaaaggttttttttaaccatctctt
 800 tcccatggtgctttcttttgggggactctagttgtttttgttttgttttattgttttacttagaaggacacacaagacacattgttatctttcttcttct
 900 tattgtagtcataagagtgaaaacccaaccatgagctgagacagaccgctcctaacttttctatggcctgagacccagctcctgttattctgttctgtt
1000 ttcttttttctttttttaatttatttattttatgtatgtgagtacagtgtcactgtcttcagacacaccagaagagggtgtcagatcccattacagatggtt
1100 gtgagccaccatgtggttgctgggaattgaactcgggacctctggaagagcagtcagtgctcttaaccgctgagccatctttccagcccctgttctgttt
1200 tcttaaataccactcccccactccacaatgtacctctatctctgggcagctgcagagccctggcctgcaatgggctaggtgacttcacactcagtctgtc
1300 atgccatccccgaaacaccacgagatataaatggttgctattgaaagctaaggaggaaaatctcagtgacgccgaaactctggaagagtggagcagattc
1400 ttcgagaggggctgggggctgggggctgggggctggagccactgttttatctcagtctgttgtttccacag
                                                                      GGGACATACCACCTGGAATCAGAAACACC
                                                                       G  D  I  P  P  G  I  R  N  T
1500 GTGTGCTTCATGCAGCGGGGCCACTGTAGGCTCTTCATGTGCCGTTCTGGGGAGAGAAAGGGCGATATTTGCTCTGACCCCTGGAACAGATGCTGCGTAT
      V  C  F  M  Q  R  G  H  C  R  L  F  M  C  R  S  G  E  R  K  G  D  I  C  S  D  P  W  N  R  C  C  V
1600 CCAGTTCCATTAAAAACAGATGATAGAAGACTCATTGGAAGATCTGAGATGTGGGGTGCAAGCTCTTGGAAGCTAGAGACCTGGAAGCACCCCAAAGGCT
      S  S  S  I  K  N  R  *  *
1700 TTGAGTATGTGTGGCTAATGGTGCGTGCTCAATAAACACTTGCTG
```

FIG. 2A

```
                       20              40              60              80
Bin1b    MKV-LLLFAVFFCLVQRNSG------DIPPGIRNTVCFMQRGHCRLFMCRSGERKGDICSDPWNRCCVSSSIKNR-----------
EP2E     MKV-FFLPAVLFCLVQTNSG------DVPLGIRNTICRMQQGICRLFFCHSGEKKRDICSDPWNRCCVSNTDEEGKEKPEMDGRSGI
BNBD9    --------------------------PEGVRNFVTCRINRGFCVPIRCPGHRRQIGTCLGPQICCR-----------------
BNBD3    --------------------------PECVRNHVTCRINRGFCVPIRCPGRTRQIGTCFGPRICCRSW---------------
BNBD7    --------------------------PEGVRNFVTCRINRGFCVPIRCPGHRRQIGTCLGPRICCR-----------------
TAP      MRLHHLLLALLFLVLSAWSG------FTQGVGNPVSCVRNKGICVPIRCPGSMKQIGTCVGRAICCRKK--------------
LAP      MRLHHLLLALLFLVLSAGSG------FTQGVRNSQSCRRNKGICVPIRCPGSMRQIGTCLGAQICCRRK--------------
EBD      MRLHHLLLTLLFLVLSAGSG------FTQGISNPLSCRLNKGICVPIRCPGNLRQIGTCFTPSVICCRWR-------------
HBD1     MRTSYLLLFTLCLLLSEMASGGNFLTGLGHRSDHYNCVSSGGQCLYSACPIFTKIQGTCYRGKAKCCK---------------
HBD2     MRVLYLLFSFLFIFLMPLPG------VFGGTGDPVTCLKSGAICHPVFCPRRYKQIGTCGLPGTICCKKP-------------
HBD3     MRIHYLLFALLFLFLVPVPGHG----GIINTLQKYYCRVRGGRCAVLSCLPKEEDIGKCSTRGRKCCRRKK------------
CBD1     MRTSYLLLFTLCLLLSEMASGGNFLTGLGHRSDHYNCVSSGGQCLYSACPIFTKIQGTCYRGKAKCCK---------------
CBD2     MRVLYLLFSFLFIFLMPLPG------VFGGTSDPVTCLKSGAICHPVFCPRRYKQIGTCGLPGTICCKKP-------------
MBD1     MKTHYFLLVMICLFSQMEPGVGILTSLGRRTDQYKCLQHGGFCLRSSCPSNTKLQGTCKPDKPNCCKS---------------
MBD2     MRTLCSLLLICCLFSYTTPAVGSLKSIGYEABLDHCHTNGGYCVRAICPPSARRPGSCFPEKNPCCKYMK-------------
MBD3     MRIHYLLFAFLLVLLSPPAA------FSKKTNNPVSCLRKGGRCWNR-CIGNTRQIGSCGVPFICCRKK--------------
MBD4     MRIHYLLFTFLLVLLSPLAA------FTQITNNPITCMTNGAICWGP-CPTAFRQIGNCGHFKICCKIR--------------
FBD1     MKTHYFLLVMLFFIFSQMELGAGILTSLGRRTDQYRCLQNGGFCLRSSCPSHTKLQGTCKPDKPNCCRS--------------
FBD2     MRIHYLLFSFLLVLLSPLSA------FTQSTNNPITCLTKGGVCWGP-CTGGFRQIGTCGLPRVICCKKK-------------
CBD1     MRLHHLLLVLFFLVLSAGSG------FTQGIRSRRSCHRNKGVCALTRCPRNMRQIGTCFGPPICCRKK--------------
CBD2     MRLHHLLLALFFLVLSAGSG------FTQGIINHRSCYRNKGVCAPARCPRNMRQIGTCHGPPICCRKK--------------
SBD1     MRLHHLLLVLFFVVLSAGSG------FTQGVRNRLSCHRNKGVCVPSRCPRHMRQIGTCRGPPICCRKK--------------
SBD2     MRLHHLLLVLFFVVLSAGSG------FTHGVTDSLSCRWKKGICVLTRCPGTMRQIGTCFGPPICCRLK--------------
IBD1     MRLHRLLLVFLLMVLLPVPG------LLKNIGNSVSCLRNKGVCMPGKCAPKMKQIGTCGMPQVICCRKK-------------
Call     ------------------------------GRKSDCFRKSGFCAFLKCPSLTLISGKCSRFYI-CCKRIW------------
Call1a   ------------------------------GRKSDCFRKNGFCAFLKCPYLTLISGKCSRFHI-CCKRIW------------
Call2    ------------------------LFC--KGGSCHFGGCPSHLIKVGSCFGFRS-CCKWPWNA------------------
THP1     MRIVYLLFPFFLLLAQGAAG------SSLALGKREKCLRRNGFCAFLKCPTLSVISGTCSRFQI-CCKTLLG-----------
THP2     MRILYLLFSLLFLALQVS------PGLSSPKRDMLFC--KRGTCHFGRCPSHLIKVGSCFGRS-CCKWPWDA-----------
         m   1                       c  g C  Cp   g C     cc
```

FIG. 2B

```
                       20              40              60
Bin1b    MKVLLLFAVFFCLVQRNS---------------------------------
EP2E     MKVFFLFAVLFCLVQTNS---------------------------------
EP2D     MRQRLLPSVLSLLLVALLFPGSSQARHVNHSATEALGERBRAFGCGNGQLRRUAMRDLLPPR
HE2b1    MRQRLLPSVLSLLLVALLFPGSSQARHVNHSATEALGERBRAFGGGTHGQLLRHAMTRQLSPRR 80             100             120
Bin1b    ----GDIPPGIRNTVCFMQRGHCRLFMCRSGERKGDICSDPWNRCCVSSSIKNR-----------
EP2E     ----GDVPLGIRNTICRMQQGICRLFFCHSGEKKRDICSDPWNRCCVSNTDEEGKEKPEMDGRSGI
EP2D     PPYQGDVPLGIRNTICRMQQGICRLFFCHSGEKKRDICSDPWNRCCVSNTDEEGKEKPEMDGRSGI
HE2b1    PPYQGDVPPGIRNTICRMQQGICRLFFCHSGEKKRDICSDPWNRCCVSNTDEEGKEKPEMDGRSGI
```

FIG. 2C

FIG. 3A
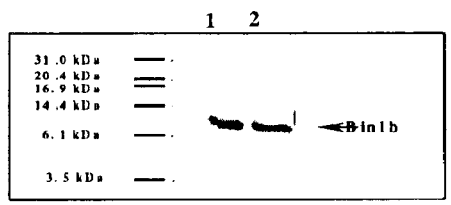
FIG. 3B
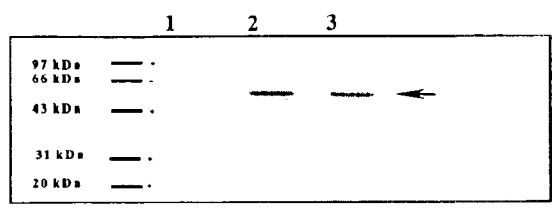
FIG. 3C
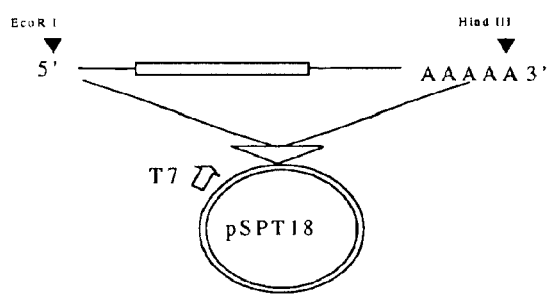
FIG. 4

FIG. 5A
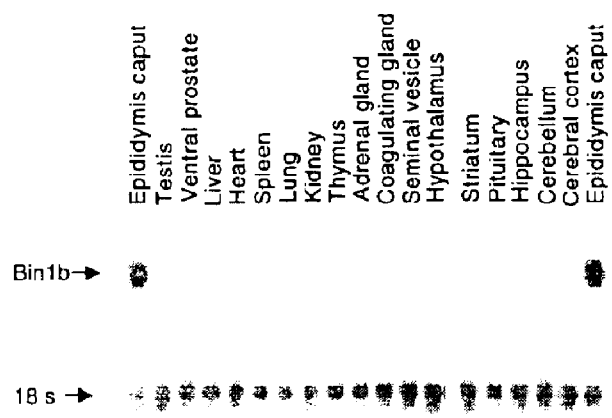
FIG. 5B
FIG. 5C
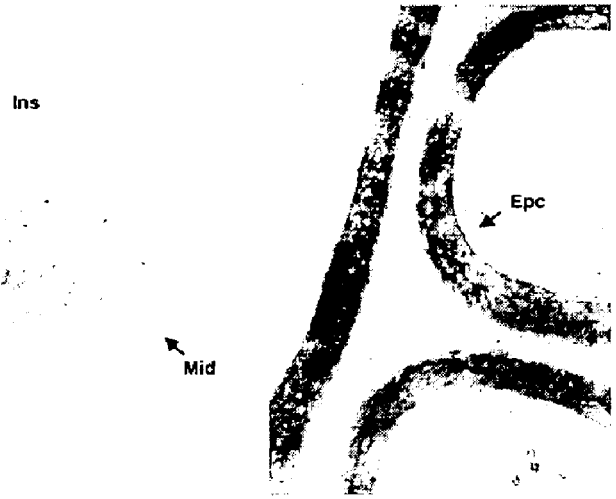

SEQUENCE LISTING

<160> NUMBER OF SEQ ID NOS: 10

<210> SEQ ID NO 1
<211> LENGTH: 385
<212> TYPE: DNA
<213> ORGANISM: Homo sapiens

<400> SEQUENCE: 1

```
ggacacccag tcatcagtca catctgcttt cctgcacaga gagagcgcca taaaacatga      60
aggttttgtt actctttgct gttttcttct gcttggtcca aagaaactca ggggacatac     120
cacctggaat cagaaacacc gtgtgcttca tgcagcgggg ccactgtagg ctcttcatgt     180
gccgttctgg ggagagaaag ggggatattt gctctgaccc ctggaacaga tgctgcgtat     240
ccagttccat taaaaacaga tgatagaaga ctcattggaa gatctgagat gtggggtgca     300
agctcttgga agctagagac ctggaagcac cccaaaggct ttgagtatgt gtggctaatg     360
gtgcgtgctc aataaacact tgctg                                           385
```

<210> SEQ ID NO 2
<211> LENGTH: 68
<212> TYPE: PRT
<213> ORGANISM: Homo sapiens

<400> SEQUENCE: 2

```
Met Lys Val Leu Leu Leu Phe Ala Val Phe Phe Cys Leu Val Gln Arg
1               5                   10                  15

Asn Ser Gly Asp Ile Pro Pro Gly Ile Arg Asn Thr Val Cys Phe Met
            20                  25                  30

Gln Arg Gly His Cys Arg Leu Phe Met Cys Arg Ser Gly Glu Arg Lys
        35                  40                  45

Gly Asp Ile Cys Ser Asp Pro Trp Asn Arg Cys Cys Val Ser Ser Ser
    50                  55                  60
```

Ile Lys Asn Arg
65

<210> SEQ ID NO 3
<211> LENGTH: 45
<212> TYPE: PRT
<213> ORGANISM: Homo sapiens

<400> SEQUENCE: 3

Gly Ile Arg Asn Thr Val Cys Phe Met Gln Arg Gly His Cys Arg Leu
1               5                   10                  15

Phe Met Cys Arg Ser Gly Glu Arg Lys Gly Asp Ile Cys Ser Asp Pro
            20                  25                  30

Trp Asn Arg Cys Cys Val Ser Ser Ile Lys Asn Arg
        35                  40                  45

<210> SEQ ID NO 4
<211> LENGTH: 1696
<212> TYPE: DNA
<213> ORGANISM: Homo sapiens

<400> SEQUENCE: 4

```
ggacacccag tcatcagtca catctgcttt cctgcacaga gagagcgcca taaaacatga      60
aggttttgtt actctttgct gttttcttct gcttggtcca agaaactca ggtaaatgtc      120 ttctgagtag ccctggagaa ggcaggatgc ccttttaggt ttgtagacca cattgaggtg     180
tgtccaggta tcaacattgg gcacagatgg tgggccactc tggggctcag ggtcggacca     240
ctttcctaac gaagaggttt tattttgatt ttttttttgtt tgttcatttg tcaagagttg    300
caaattttac agcacggaga cacagaggcc tatattctcc attgtgaata gaaggtctg     360 attgtaactt gagagtttat tcaggacaga attacagccg tacctgtgtc aaaagtgtaa     420
ttttactgcc tcgctgtgag cagagaaggt gttcacattt atgccccttc cctacccatt     480
acatccacag aacaccagat gtatgcttta aatgaatttt caaatgagag aaaaataggt     540
tcctttaaga aagctagagt ccaggtcctg aagccttgaa ttgctggcag ttctgtcaag     600
gtggactaca cccacatctc catgaacctt cccaaccatg gtaaaccgga tgaacacagt      660
atcacaaatc agtccccagc tgaagtccgg ctattgcagg agaccagttt cctaaatgtt     720
acaggcatag gttgggccgc tgttgctttt taacacaggg tgtgcaacat tgttaaaaag     780 gttttttttta accatctctt tcccatggtc ctttcttttg ggggactcta gttgttttg     840 ttttgttttta ttgttttact tagaaggaca cacaagacac attgttatct tcttcttct    900 tattgtagtc ataagagtga aaacccaacc atgagctgag acagaccgc tcctaacttt      960 tctatggcct gagacccagc tcctgttatt ctgttctgtt ttcttttct tttttaattt     1020 atttatttta tgtatgtgag tacagtgtca ctgtcttcag acacaccaga agagggtgtc    1080
agatcccatt acagatggtt gtgagccacc atgtggttgc tgggaattga actcgggacc    1140
tctggaagag cagtcagtgc tcttaaccgc tgagccatct ttccagcccc tgttctgttt   1200
tcttaaatac cactcccca ctccacaatg tacctctatc tctgggcagc tgcagagccc    1260
tggcctgcaa tgggctaggt gacttcacac tcagtctgtc atgccatccc cgaaacacca    1320
cgagatataa atggttgcta ttgaaagcta aggaggaaaa tctcagtgac gccgaaactc    1380
tggaagagtg gagcagattc ttcgagaggg gctggggggct gggggctggg ggctggagcc   1440
actgttttat ctcagtctgt tgtttccaca ggggacatac cacctggaat cagaaacacc    1500
```

-continued gtgtgcttca tgcagcgggg ccactgtagg ctcttcatgt gccgttctgg ggagagaaag    1560 ggggatatt gctctgaccc ctggaacaga tgctgcgtat ccagttccat taaaaacaga    1620
tgatagaaga ctcattggaa gatctgagat gtggggtgca agctcttgga agctagagac   1680
ctggaagcac cccaaa                                                    1696

<210> SEQ ID NO 5
<211> LENGTH: 21
<212> TYPE: DNA
<213> ORGANISM: Artificial sequence
<220> FEATURE:
<221> NAME/KEY: misc_feature
<223> OTHER INFORMATION: primer

<400> SEQUENCE: 5
aatggtaccg tgacgtggtc c                                              21

<210> SEQ ID NO 6
<211> LENGTH: 21
<212> TYPE: DNA
<213> ORGANISM: Artificial sequence
<220> FEATURE:
<221> NAME/KEY: misc_feature
<223> OTHER INFORMATION: primer

<400> SEQUENCE: 6
tggccccgct gcatgaagca c                                              21

<210> SEQ ID NO 7
<211> LENGTH: 20
<212> TYPE: DNA
<213> ORGANISM: Artificial sequence
<220> FEATURE:
<221> NAME/KEY: misc_feature
<223> OTHER INFORMATION: primer

<400> SEQUENCE: 7
ggacacccag tcatcagtca                                                20

<210> SEQ ID NO 8
<211> LENGTH: 20
<212> TYPE: DNA
<213> ORGANISM: Artificial sequence
<220> FEATURE:
<221> NAME/KEY: misc_feature
<223> OTHER INFORMATION: primer

<400> SEQUENCE: 8
cagcaagtgt ttattgagca                                                20

<210> SEQ ID NO 9
<211> LENGTH: 23
<212> TYPE: DNA
<213> ORGANISM: Artificial sequence
<220> FEATURE:
<221> NAME/KEY: misc_feature
<223> OTHER INFORMATION: primer

<400> SEQUENCE: 9
ggacacccag tcatcagtca cat                                            23

<210> SEQ ID NO 10
<211> LENGTH: 22
<212> TYPE: DNA
<213> ORGANISM: Artificial sequence
<220> FEATURE:

-continued

```
<221> NAME/KEY: misc_feature
<223> OTHER INFORMATION: primer

<400> SEQUENCE: 10
tttggggtgc ttccaggtct ct                                              22
```

NATURAL ANTIBACTERIAL PEPTIDE, THE NUCLEOTIDE SEQUENCE ENCODING IT AND THE USE THEREOF

CROSS-REFERENCE TO RELATED APPLICATION(S)

This application is a Continuation of International Patent Application No. PCT/CN02/00032, filed on Jan. 21, 2002, which claims priority to earlier filed Chinese Patent Application No. 01105283.X, filed on Jan. 22, 2001, the contents of both are incorporated herein by reference.

FIELD OF INVENTION

This invention relates to molecular biology and immunology, reproductive biology and medicine. In particular, it relates to a novel natural antibacterial peptide specifically expressed in rat caput epididymidis—Bin1b protein, its encoding polynucleotide, and the preparation and uses thereof. Bin1b protein relates to male fertility, especially sperm maturation.

BACKGROUND

The sequencing of human genome describes code sequences. Which region is a gene? What is the function? Which genes are needed for a biological function? How do they cooperate in normal life? Which mistakes are the causes for diseases? This difficult, challenging, beneficial, and profitable decoding works bring us into an era of functional genomics.

At the turn of the new century, the scientists deem that although the achievements of reproductive biology are great, the prospect of development is pessimistic if only the classic methods limited to tissues and cells are used without utilizing new technologies, without studying the molecular mechanisms, and without combining different disciplines. People have focused on female reproduction and paid little attention to male reproduction. The basic researches on reproductive principles are neglected, resulting in no ideal medicine and techniques for birth control and insufficient knowledge of human reproduction. The reproductive biology encounters two revolutionary changes in the 21st century. One is to strengthen the basic researches and study the mechanism for human reproduction and birth defects by using the new methods of molecular biology, molecular immunology and cell biology. The other is to strengthen the study of male reproductive biology, thereby developing male contraceptives.

China has 22% population, only 7% cultivated land and 6% fresh water in the world. Even the growth rate is 0.01%, 13 million peoples increase each year. The contraception methods, which are imperfect and have some side effects, are mainly used by females. The safe sterilization means are also taken by females. According to WHO statistics, only $\frac{1}{12}$ males in Sichuan province are vasoligated. Actually, both men and women have responsibility of contraception. The control of male reproduction is important to human quantity and quality because (1) a healthy man produces $10^8$ sperms/day in 50 years and a woman produce 1 egg/month in 40 years, (2) the sperms are sensitive to environment, (3) the quantity and quality of sperm have decreased 40% in the last 50 years, and (4) 5–10% of males under 45 have primary sterility. To correct the bias, it is necessary to strengthen the researches and develop male contraception means. It is well-known that the health of human reproduction is important worldwide. The contraception is only a temporary measure for population crisis, and the off-springs should seek a physically and mentally healthy life. The design of birth-control medicine should suit the new needs. On Sep. 9–10, 1999, in the seminar of "male contraception in 21st century" held by NICHD in NIH headquarters, people studied the situation, put forward the objects and arranged the activities including co-operation and fund support [Trends in Endocrinology and Metabolism 2000, 11 (2):66–69].

Spermatocytes undergo mitosis, meiosis and differentiation and form sperms in testis. Then they enter into epididymis, gradually mature in caput and corpus, and deposit at cauda until ejaculation. A series of maturation changes including the motor capacity of sperm, the formation of acrosome function, the conversion of metabolism are not accomplished by sperm themselves. The sperms gradually mature by interacting with the epididymis microenvironment when passing the epididymis. Epididymis is a long, narrow and zigzag passage connecting testis and spermaductus. The cells in different parts of epididymis express different genes and products, and excrete different proteins and molecules. The different fluid components, ionic strength and pH form the changing micro-environment and interact with sperm to partially alter or modify the sperm surface protein, such as phosphorylation, esterification, acylation, carboxylation, and glycosylation. The sperms gradually obtain the functions and immunologic defense for maturation, which protect sperms in epididymis until they pass female genital tract toward ovum.

The maturation, storage and protection of epididymis have the following properties and, therefore, it is an ideal target for birth control.

(1) The function is simple. The interfering medicines are unlikely to cause severe side effects.

(2) Epididymis is a final organ for hormones and has no endocrine function. The epididymis medicines normally do not effect hormone secretion.

(3) Before entering epididymis, sperms are completely differentiated and transcription is stopped. The maturation involves protein modification but no DNA replication. The medicines are unlikely to cause DNA mutations and diseases.

(4) The study of epididymis is not emphasized and has promising potential.

The mechanism for forming the micro-environment in parts of epididymis is not determined by one or two genes and protein, but by a group of co-operating products. Little is known about the initiation and process of epididymis gene expression related to sperm maturation. The study helps to disclose the molecular mechanism of sperm maturation, decode genomic codes, establish a foundation for sperm-related infertility, and provide new routes for develop male contraception drugs which blocks sperm maturation.

Since 1970's, The researches on epididymis mainly focused on the following three aspects:

(1) Some results have been obtained on protein level by comparing the proteins in the lumen at different parts of epididymis or the differently maturated membrane proteins of sperm at different parts through dielectrophoresis, or by comparing them in immunoassay using polyclonal antibodies against proteins. However, the developments are dissatisfactory due to low sensitivity of separation or analysis technology. The Dacheux Laboratory (France) has reported the identification of more than 200 proteins from the lumen of epididymis of swine and sheep, indicating the research on epididymis is less difficult than the other organs. However, only 15 epididymis specific cDNAs have been cloned.

(2) The known roles of epididymis in sperm maturation may be used to determine whether the specific function of epididymis is related to some known proteins. For example, it is known that epididymis protects sperms from damage caused by oxygen free-radical. The mRNAs of six antioxidases on different parts of epididymis have been detected. E-GPX and E-SOD have the highest amount of mRNA at caput and corpus, respectively, indicating that the different parts of epididymis need different antioxidases. However, those researches are restricted to the known knowledge and hardly helpful to find new function genes or products. Additionally, there are many immunocytes and immunodepressive molecules in epididymis, which forms a protecting immunological micro-environment. However, the molecules and cellular mechanism for the formation and regulation are unclear.

(3) The molecular biochemistry technology develops quickly since 1990's and one can find new genes specifically expressed in epididymis on mRNA level by subtraction hybridization, etc. A German laboratory found 6 new mRNAs in human epididymis by subtraction screening of cDNA library. However, due to the limitations of the human epididymis or other materials, their functions were not intensively studied. Therefore, people study the laboratory animals by different means.

Therefore, there is an urgent need to develop new natural protein related to male reproduction and epididymis.

SUMMARY OF INVENTION

One purpose of the invention is to provide a novel antibacterial peptide-Bin1b and its fragments, analogs and derivatives.

Another purpose of the invention is to provide polynucleotides encoding the polypeptides.

Still another purpose of the invention is to provide the preparation and uses of the polypeptides and polynucleotides.

In the 1st aspect, the invention provides an isolated rat Bin1b polypeptide, which comprises a polypeptide having the amino acid sequence of SEQ ID NOs: 2 or 3, its conservative variants, its active fragments, and its active derivatives. Preferably, said polypeptide has the amino acid sequence of SEQ ID NOs: 2 or 3.

In the 2nd aspect, it provides an isolated polynucleotide comprising a nucleotide sequence sharing at least 70% identity to the following nucleotide sequences: (a) the polynucleotide encoding Bin1b polypeptide of SEQ ID NOs: 2 or 3; (b) the polynucleotide complementary to polynucleotide of (a). Preferably, said polynucleotide encodes a polypeptide comprising the amino acid sequence of SEQ ID NOs: 2 or 3. More preferably, said polynucleotide is selected from the group consisting of (a) 57–260 of SEQ ID NO:1; (b) 105–260 of SEQ ID NO:1; and (c) 1–336 of SEQ ID NO:1.

In the 3rd aspect, it provides a vector comprising the above polynucleotide, and a host cell transformed with the vector or polynucleotide.

In the 4th aspect, it provides a method for producing a polypeptide having the activity of Bin1b protein, which comprises:
 (a) culturing the above transformed host cell under the expression conditions;
 (b) isolating the polypeptides having the activity of Bin1b protein from the culture.

In the 5th aspect, it provides an antibody specifically binding Bin1b protein. Also provided are nucleic acid molecules comprising consecutive 15–1757 nucleotides of the above polynucleotide.

In the 6th aspect, it provides compounds that simulate, promote and antagonize Bin1b activity, or inhibit Bin1b expression and methods for screening and preparing these compounds. Preferably, the compounds are antisense sequences of Bin1b encoding sequence or fragments thereof.

In the 7th aspect, it provides a method for detecting Bin1b protein in a sample, comprising: contacting the sample with the antibody specifically against Bin1b protein, observing the formation of antibody complex which indicates the presence of Bin1b protein in the sample.

In the 8th aspect, it provides a method for determining the diseases related to Bin1b abnormal expression or the susceptibility thereof, which comprises detecting the mutation of Bin1b encoding sequence.

In the 9th aspect, it provides the uses of Bin1b and its encoding sequence, e.g., in screening Bin1b agonists and antagonist, and peptide fingerprinting. The Bin1b encoding sequence and its fragment can be used as primers in PCR, or probes in hybridization and microarray.

In the 10th aspect, it provides a pharmaceutical composition comprising a safe and efficient amount of Bin1b protein, or its agonist or antagonist and pharmaceutically acceptable carrier. This pharmaceutical composition can be used to treat diseases, e.g., urogenital infection.

In the 11th aspect, it provides a microbicide comprising an antimicrobially efficient amount of Bin1b polypeptide.

The other aspects of invention will be apparent to artisan in light of the teaching of the invention.

The inventors screened the genes specifically expressed in parts of rat and monkey epididymis by differential display and subtraction hybridization and cooperated with North Carolina University on monkey research. We not only identified the known specific genes, but also obtain full-length cDNA clones of genes specifically expressed, 2 in rat caput epididymidis, 4 in monkey epididymis caput, 4 in monkey epididymis corpus, and 3 in monkey epididymis cauda.

Bin1b, which specifically expresses in rat caput epididymidis, is one of them. The full-length cDNA and genomic DNA clones were obtained. The nucleotide and amino acid sequence were registered in Genbank of NIH with accession Nos. AF217088 and AF217089, which will be published after filing this application. Bin1b gene is expressed very specifically, only in the epithelial cells of rat caput epididymidis. It is maximally expressed in sexually mature rats and decreased in old rats, indicating Bin1b relates to reproduction. Androgens up-regulate the Bin1b expression. One may influence Bin1b expression with hormones and design male contraceptives to regulate sperm maturation. Further, Bin1b is the first natural antibacterial peptide in beta-defensin family found in rat epididymis. It has prospect of being developing into a natural drug for curing urogenital infection.

DESCRIPTION OF DRAWINGS

The following drawings illustrate the embodiments, and do not limit the scope of invention defined in the claims.

FIG. 1. DD-RT-PCR of rat epididymis caput (1), corpus (2) and cauda (3). The sample are duplicated for accuracy. Bin1b is differentially expressed in caput region as arrow indicated.

FIG. 2A. Sequence and structural characteristics of Bin1b. Genomic DNA sequence (Genebank accession number: AF217089) of Bin1b. It is cloned by PCR using primers located at both ends of the Bin1b full-length cDNA (AF217088) (upper primer 5'-GGACACCCAGTC ATCAGTCACAT-3' (SEQ ID NO:9) and lower primer 5'-TTTGGGGTGCTT CCAGGTCTCT-3' (SEQ ID NO:10)) with rat genomic DNA as template. Two exons: uppercase; Coding region: shadowed portion; PolyA signal: bold uppercase; Intron: lowercase; Splicing site: bold lowercase; Putative signal peptide: amino acids underlined. The potential N-terminal is a myristoylated G residue in box whose consensus pattern (GIRNTV) is in bold italic uppercase and S residue in circle may be phosphorylated by PKC whose consensus pattern (SIK) is in bold italic uppercase. Stop codon is designated by *.

FIG. 2B. Sequence Similarity of Bin1b with (-defensins. The conserved six Cysteine residues in (-defensins are shadowed. BNBD9 (AAB25872), BNBD3 (AAB25866), BNBD7 (AAB25870), TAP (P25068), LAP (Q28880), EBD (O02775) from cattle; HBD1 (Q09753), HBD2 (O15263), HBD3 (NP061131) from human; EP2E (AF263555_1) CBD1 (AF188607_1), CBD2 (AF209855_1) from Chimpanzee; MBD1 (AAB72003), MBD2 (CAB42815), MBD3 (AF092929_1), MBD4 (AF155882_1) from mouse; RBD1 (AAC28071), RBD2 (AAC28072) from rat; GBD1 (CAA76811), GBD2 (CAA08905) from goat; SBD1 (O19038), SBD2 (O19039) from sheep; PBD1 (O62697) from pig; Gal1 (P46156), Galla (P46157) and Gal2 (P46158) are chicken gallinacin 1, 1 (and 2 respectively; THP1 (P80391) and THP2 (P80392) are turkey heterophil peptide 1 and 2 respectively. EP2E is one of the chimpanzee homologs of Bin1b, which was not considered as a member of (-defensin family by its original authors.

FIG. 2C. Alignment of Bin1b with its primate homologs. Compared to Bin1b, its primate homolog EP2D (AF263554_1) and HE2 (1 (AF168617_1) have an extended N-terminal and C-terminal and EP2E (AF262555_1) has only extended C-terminal. HE2 (1 is designated as HE2b1 in the figure.

FIG. 3. In vitro transcription and translation assay of Bin1b full-length cDNA.

FIG. 3A. In vitro transcription and translation assay of Bin1b full-length cDNA. Lanes 1 and 2 are duplicate samples.

FIG. 3B. Negative control (no plasmid DNA) and luciferase SP6 and T7 control are assayed in the same system as 3A. but run in 12% SDS-PAGE gel because of molecular weight differences. Lane 1. Negative control (no plasmid DNA). Lane2. Luciferase SP6 control. Lane 3. Luciferase T7 control.

FIG. 3C. Construction of pSPT18-Bin1b.

FIG. 4. Recombinant Fusion Expression of Bin1b. The fusion protein DHFR-Bin1b is 31 KD as indicated by the arrow. NI: non-induced, I: induced, CL: clear lysate, FT: flow through, W: wash buffer, E1: elution 1, E2: elution 2, M: marker.

FIG. 5. Localization and developmental regulation of Bin1b.

FIG. 5A. Tissue distribution of Bin1b by Northern analysis.

FIG. 5B. Regional distribution of Bin1b in the epididymis by in situ hybridization. Bin1b is located in middle (Mid) of the rat epididymis caput region. Ins: initial segment.

FIG. 5C. Cellular localization of Bin1b using antisense probe. Bin1b is located in the principle cells (Prc) of the epididymis.

FIG. 6. Northern blot analysis of rat epididymis caput total RNA after Ethylene Dinethamesulfonate (EDS) treatment.

FIG. 7. Antimicrobial activity of Bin1b and its expression upregulation in response to inflammation.

DETAILED DESCRIPTION

Figures 5D, 5E:
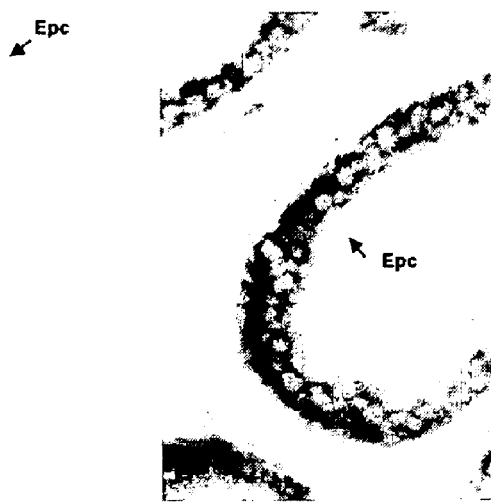
FIG. 5D. Sense probe.
FIG. 5E. 18s probe as positive control.

As used herein, the term "Bin1b protein", "Bin1b polypeptide" or "antimicrobial peptide Bin1b" are exchangeable, referring to a protein or polypeptide comprising the amino acid sequence of natural antimicrobial peptide Bin1b (SEQ ID NOs: 2 or 3). The term includes Bin1b with or without the starting Met residue, Bin1b with or without signal peptide. The mature Bin1b is shown in SEQ ID NO:3.

As used herein, the term "isolated" refers to a substance which has been isolated from the original environment. For naturally occurring substance, the original environment is the natural environment. E.g., the polynucleotide and polypeptide in a naturally occurring state in the viable cells are not isolated or purified. However, if the same polynucleotide and polypeptide have been isolated from other components naturally accompanying them, they are isolated or purified. "Isolation" and "purification" include separating recombinant Bin1b protein from other proteins, saccharide, etc.

As used herein, the terms "isolated Bin1b protein or polypeptide" mean that Bin1b polypeptide does not essentially contain other proteins, lipids, carbohydrate or any other substances associated therewith in nature. The artisans can purify Bin1b protein by standard protein purification techniques.

The polypeptide of invention may be a recombinant, natural, or synthetic polypeptide, preferably a recombinant polypeptide. The polypeptide of invention may be a purified natural product or a chemically synthetic product. Alternatively, it may be produced from prokaryotic or eukaryotic hosts, such as bacteria, yeast, higher plant, insect, and mammalian cells, using recombinant techniques. According to the host used in the recombinant production, the polypeptide may be glycosylated or non-glycosylated. The polypeptide may or may not comprise the starting Met residue.

The invention further comprises the fragments, derivatives and analogues of Bin1b. As used in the invention, the terms "fragment", "derivative" and "analogue" mean the polypeptide that essentially retains the same biological functions or activity of natural Bin1b protein. The fragment, derivative or analogue of the polypeptide may be (i) one in which one or more of the amino acid residues are substituted with a conserved or non-conserved amino acid residue (preferably a conserved amino acid residue), or (ii) one in which one or more of the amino acid residues include a substituent group, or (iii) one in which the mature polypeptide is fused with another compound, such as a compound to increase the half-life of the polypeptide (for example, polyethylene glycol), or (iv) one in which the additional amino acids are fused to mature polypeptide, such as a leader or secretary sequence or a sequence used for purifying polypeptide or proprotein, e.g., a fusion protein formed with IgC fragment. Such fragments, derivatives and analogs are known to the artisans based on the teachings herein.

The particular Bin1b analogs are homologous proteins in other mammals, e.g., cow, sheep, rabbit, dog, monkey, human, etc. One can obtain the sequences encoding these homologous proteins by hybridization or amplification based on the disclosed sequence herein, and obtain the proteins using conventional recombinant techniques.

In the present invention, the term "Bin1b polypeptide" means a polypeptide having the activity of Bin1b protein comprising the amino acid sequence of SEQ ID NOs: 2 or 3. The term also comprises the variants which have the same function of Bin1b. These variants include, but are not limited to, deletions, insertions and/or substitutions of several amino acids (typically 1–20, preferably 1–10, more preferably 1–5, most preferably 1–3), and addition of one or more amino acids (typically less than 20, preferably less than 10, more preferably less than 5) at C-terminal and/or N-terminal. E.g., the protein functions are usually unchanged when an amino residue is substituted by a similar or analogous one. Further, the addition of one or several amino acids at C-terminal and/or N-terminal usually does not change the protein function. The term also includes the active fragments and derivatives of Bin1b protein.

The variants of polypeptide include homologous sequences, conservative mutants, allelic variants, natural mutants, induced mutants, proteins encoded by DNA which hybridizes to Bin1b DNA under high or low stringency conditions as well as the polypeptides retrieved by antisera raised against Bin1b polypeptide. The present invention also provides other polypeptides, e.g., fusion proteins, which include the Bin1b polypeptide or fragments thereof. Besides substantially full-length polypeptide, the soluble fragments of Bin1b polypeptide are also included. Generally, these fragments comprise at least 15, typically at least 25, preferably at least 35, more preferably at least 40 consecutive amino acids of Bin1b polypeptide.

The invention also provides the analogues of Bin1b polypeptide. Analogues can differ from naturally occurring Bin1b polypeptide by amino acid sequence differences or by modifications which do not affect the sequence, or by both. These polypeptides include genetic variants, both natural and induced. Induced variants can be made by various techniques, e.g., by random mutagenesis using irradiation or exposure to mutagens, or by site-directed mutagenesis or other known molecular biologic techniques. Also included are analogues which include residues other than those naturally occurring L-amino acids (e.g., D-amino acids) or non-naturally occurring or synthetic amino acids (e.g., beta- or gamma-amino acids). It is understood that the polypeptides of the invention are not limited to the representative polypeptides listed hereinabove.

Modifications (which do not normally alter primary sequence) include in vivo or in vitro chemical derivation of polypeptides, e.g., acelylation, or carboxylation. Also included are modifications of glycosylation, e.g., those made by modifying the glycosylation patterns of a polypeptide during its synthesis and processing or in the further processing steps, e.g., by exposing the polypeptide to glycosylation enzymes (e.g., mammalian glycosylating or deglycosylating enzymes). Also included are sequences having phosphorylated amino acid residues, e.g., phosphotyrosine, phosphoserine, phosphothronine, as well as sequences modified to improve the resistance to proteolytic degradation or to optimize solubility properties.

In the invention, "Bin1b conservative mutant" means a polypeptide formed by substituting at most 10, preferably at most 8, more preferably 5, and most preferably at most 3 amino acids with the amino acids having substantially the same or similar property, as compared with the amino acid sequence of SEQ ID NOs: 2 or 3. Preferably, these conservative mutants are formed by the substitution according to Table 1.

TABLE 1

| Initial residue | Representative substitution | Preferred substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The polynucleotide of invention may be in the forms of DNA and RNA. DNA includes cDNA, genomic DNA, and synthetic DNA, etc., in single strand or double strand form. A single strand DNA may be an encoding strand or non-encoding strand. The coding sequence for mature polypeptide may be identical to the coding sequence shown in SEQ ID NO:1, or is a degenerate sequence. As used herein, the term "degenerate sequence" means an sequence which encodes a protein comprising the sequence of SEQ ID NOs: 2 or 3 and which has a nucleotide sequence different from the coding region in SEQ ID NO:1.

The sequences encoding the mature polypeptide include those encoding only the mature polypeptide, those encoding mature polypeptide plus various additional encoding sequence, the encoding sequence for mature polypeptide plus the non-encoding sequence and optional additional encoding sequence.

The term "polynucleotide encoding the polypeptide" includes the polynucleotide encoding said polypeptide and the polynucleotide comprising additional and/or non-encoding sequence.

The invention further relates to the variants of polynucleotides which encode a polypeptide having the same amino acid sequence, or its fragment, analogue and derivative. The variant of the polynucleotide may be a naturally occurring allelic variant or a non-naturally occurring variant. Such nucleotide variants include substitution, deletion, and insertion variants. As known in the art, the allelic variant is a substitution form of polynucleotide, which may be a substitution, deletion, and insertion of one or more nucleotides without substantially changing the functions of the encoded polypeptide.

The invention further relates to polynucleotides, which hybridize to the hereinabove-described sequences, if there is at least 50%, preferably at least 70%, and more preferably at least 80% between the sequences. The invention particularly relates to polynucleotides, which hybridize under stringent conditions to the polynucleotides of the invention. As herein used, the term "stringent conditions" means the following conditions: (1) hybridization and washing under low ionic strength and high temperature, such as 0.2× SSC, 0.1% SDS, 60° C.; (2) hybridization after adding denaturants, such as 50% (v/v) formamide, 0.1% bovine serum/0.1% Ficoll, 42° C.; or (3) hybridization of two sequences sharing at least 95%, preferably 97% homology. Further, the hybridizing polynucleotides encode a polypeptide which retains the same biological function or activity as the mature polypeptide of SEQ ID NO:2

The invention also relates to nucleic acid fragments hybridized with the hereinabove sequence. As used herein, the length of "nucleic acid fragment" is at least 15 bp, preferably 30 bp, more preferably 50 bp, and most preferably at least 100 bp. These fragments can be used in the amplification techniques of nucleic acid, e.g., PCR, to determine and/or isolate the Bin1b encoding polynucleotide.

The full-length Bin1b nucleotide sequence or its fragment can be prepared by PCR amplification, recombinant method and synthetic method. For PCR amplification, one can obtain said sequences by designing primers based on the nucleotide sequence disclosed herein, especially the ORF, and using cDNA library commercially available or prepared by routine techniques in the art as a template. When the sequence is long, it is usually necessary to perform two or more PCR amplifications and link the amplified fragments together correctly.

Once the sequence is obtained, one can produce lots of the sequences by recombinant methods. Usually, said sequence is cloned into a vector which is then transformed into a host cell. The sequence is isolated from the amplified host cells using conventional techniques.

Further, the sequence can be synthesized because Bin1b sequence is short. Typically, several small fragments are synthesized and linked together to obtain a long sequence.

It is completely feasible to chemically synthesize the DNA sequence encoding the protein of invention, or the fragments or derivatives thereof. In addition, the mutation can be introduced into the protein sequence by chemical synthesis.

The amplification of DNA/RNA by PCR (Saiki, et al. Science 1985; 230:1350–1354) is preferably used to obtain Bin1b gene. Especially when it is difficult to obtain the full-length cDNA, RACE is preferably used. The primers used in PCR can be properly selected according to the sequence information disclosed herein and synthesized by the conventional methods. The amplified DNA/RNA fragments can be isolated and purified by conventional methods, e.g., gel electrophoresis.

The invention further relates to a vector comprising the polynucleotide of invention, a genetic engineered host cell transformed with the vector or the sequence encoding Bin1b protein, and the method for producing the Bin1b polypeptide by recombinant techniques.

The recombinant Bin1b polypeptides can be expressed or produced by the conventional recombinant DNA technology (Science, 1984; 224:1431), using the polynucleotide sequence of invention. Generally, it comprises the following steps:

(1) transfecting or transforming the appropriate host cells with the polynucleotide encoding Bin1b polypeptide or the vector containing the polynucleotide;

(2) culturing the host cells in an appropriate medium;

(3) isolating or purifying the protein from the medium or cells.

In the invention, the polynucleotide sequences encoding Bin1b may be inserted into a recombinant expression vector. The term "expression vector" means a bacterial plasmid, bacteriophage, yeast plasmid, plant virus or mammalian cell virus, such as adenovirus, retrovirus or any other vehicles known in the art. Any plasmid or vector can be used to construct the recombinant expression vector as long as it can replicate and is stable in the host. One important feature of expression vector is that the expression vector typically contains a replication origin, a promoter, a marker gene as well as the translation regulatory components.

The known methods can be used to construct an expression vector containing Bin1b DNA sequence and appropriate transcription/translation regulatory components. These methods include in vitro recombinant DNA technique, DNA synthesis technique, in vivo recombinant technique, etc. The DNA sequence is efficiently linked to the proper promoter in an expression vector to direct the synthesis of mRNA. The exemplary promoters are lac or trp promoter of E. coli; $P_L$ promoter of λ phage; eukaryotic promoter including CMV immediate early promoter, HSV thymidine kinase promoter, early and late SV40 promoter, LTRs of retrovirus and some other known promoters which control the gene expression in the prokaryotic cells, eukaryotic cells or virus. The expression vector may further comprise a ribosome-binding site for initiating the translation, transcription terminator and the like.

The expression vector preferably comprises one or more selective marker genes to provide a phenotype for selecting the transformed host cells, e.g., the dehydrofolate reductase, neomycin resistance gene and GFP (green flurencent protein) for eukaryotic cells, as well as tetracycline or ampicillin resistance gene for E. coli.

The vector containing said DNA sequence and proper promoter or regulatory elements can be transformed into appropriate host cells to express the protein.

The "host cell" includes prokaryote, e.g., bacteria; primary eukaryote, e.g., yeast; advanced eukaryotic, e.g., mammalian cells. The representative examples are bacterial cells, e.g., E. coli, Streptomyces, Salmonella typhimurium; fungal cells, e.g., yeast; plant cells; insect cells e.g., Drosophila S2 or Sf9; animal cells e.g., CHO, COS or Bowes melanoma, etc.

Transcription of the polynucleotide in higher eukaryotes is increased by inserting an enhancer sequence into the vector. Enhancers are cis-acting elements of DNA, usually about 10–300 bps, that act on a promoter to increase gene transcription. Examples include SV40 enhancer on the late side of replication origin 100 to 270 bp, the polyoma enhancer on the late side of replication origin, and adenovirus enhancers.

The artisans know clearly how to select appropriate vectors, promoters, enhancers and host cells.

Recombinant transformation of host cell with the DNA might be carried out by conventional techniques known to the artisans. Where the host is prokaryotic, e.g., *E. coli*, the competent cells capable of DNA uptake, can be prepared from cells harvested after exponential growth phase and subsequently treated by the $CaCl_2$ method using known procedures. Alternatively, $MgCl_2$ can be used. The transformation can also be carried out by electroporation. When the host is an eukaryote, transfection of DNA such as calcium phosphate co-precipitates, conventional mechanical procedures e.g., micro-injection, electroporation, or liposome-mediated transfection may be used.

The transformants are cultured conventionally to express Bin1b polypeptide. According to the used host cells, the medium for cultivation can be selected from various conventional mediums. The host cells are cultured under a condition suitable for its growth until the host cells grow to an appropriate cell density. Then, the selected promoter is induced by appropriate means (e.g., temperature shift or chemical induction) and cells are cultured for an additional period.

In the above methods, the recombinant polypeptide may be included in the cells, or expressed on the cell membrane, or secreted out. If desired, the physical, chemical and other properties can be utilized in various isolation methods to isolate and purify the recombinant protein. These methods are well-known to the artisans and include, but are not limited to conventional renaturation treatment, treatment by protein precipitant (e.g., salt precipitation), centrifugation, cell lysis by osmosis, sonication, supercentrifugation, molecular sieve chromatography or gel chromatography, adsorption chromatography, ion exchange chromatagraphy, HPLC, and any other liquid chromatagraphy, and the combination thereof.

The recombinant Bin1b polypeptide have various uses including, but not limited to: curing urogenital infection, and screening out antibodies, polypeptides or ligands as agonists or antagonists of Bin1b. The expressed Bin1b protein can be used to screen polypeptide library to find out therapeutically valuable polypeptide molecules which inhibit or activate Bin1b protein.

In another aspect, the invention also includes polyclonal and monoclonal antibodies (mAbs), preferably mAbs, which are specific for polypeptides encoded by Bin1b DNA or fragments thereof. By "specificity", it means an antibody which binds to the Bin1b gene products or a fragments thereof. Preferably, the antibody binds to the Bin1b gene products or fragments thereof and does not substantially recognize nor bind to other antigenically unrelated molecules. Antibodies which bind to Bin1b and block Bin1b protein and those which do not affect the Bin1b function are included in the invention.

The invention includes intact monoclonal or polyclonal antibodies, and immunologically-active antibody fragments, e.g., a Fab' or (Fab)$_2$ fragment, an antibody heavy chain, an antibody light chain, or a chimeric antibody.

The antibodies in the present invention can be prepared by various techniques known in the art. E.g., purified Bin1b gene products, or its antigenic fragments can be administrated to animals (e.g., rabbit, mice and rat) to produce polyclonal antibodies. Similarly, cells expressing Bin1b or its antigenic fragments can be used to immunize animals to produce antibodies. Various adjuvants, e.g., Freund's adjuvant, can be used to enhance immunization.

The mAbs can be prepared using hybridoma technique (Kohler et al., *Nature* 256;495, 1975; Kohler et al., *Eur-.J.Immunol.* 6:511, 1976; Kohler et al., *Eur.J.Immunol.* 6:292, 1976; Hammerling et al., *In Monoclonal Antibodies and T Cell Hybridomas*, Elsevier, N.Y., 1981). Antibodies comprise those which block Bin1b function and those which do not affect Bin1b function. Antibodies can be produced by routine immunology techniques and using fragments or functional regions of Bin1b gene product prepared by recombinant methods or synthesized by a polypeptide synthesizer. The antibodies binding to unmodified Bin1b gene product can be produced by immunizing animals with gene products produced by prokaryotic cells (e.g., *E. coli*), and the antibodies binding to post-translationally modified forms thereof can be acquired by immunizing animals with gene products produced by eukaryotic cells (e.g., yeast or insect cells).

The antibody against Bin1b can be used in immunohistochemical method to detect the presence of Bin1b protein in biopsy specimen. The mAb can be radiolabelled and injected into body to trace the position and distribution of Bin1b.

The substances which act with Bin1b protein, e.g., receptors, inhibitors, agonists and antagonists, can be screened out by various conventional techniques, using Bin1b protein.

The Bin1b protein, antibody, inhibitor, agonist or antagonist of the invention provide different effects when administrated in therapy. Usually, these substances are formulated with a non-toxic, inert and pharmaceutically acceptable aqueous carrier. The pH typically is about 5–8, preferably 6–8, although pH may alter according to the property of the formulated substances and the diseases to be treated. The formulated pharmaceutical composition is administrated in conventional routes including, but not limited to, intramuscular, intravenous, subcutaneous, intradermal or topical administration.

The Bin1b polypeptide can be directly used for curing disorders, e.g., urogenital infection. The Bin1b protein can be administrated in combination with other medicaments, e.g, antibiotics including penicillin.

The invention also provides a pharmaceutical composition comprising safe and effective amount of Bin1b protein in combination with a pharmaceutically acceptable carrier. Such a carrier includes but is not limited to saline, buffer solution, glucose, water, glycerin, ethanol, or the combination thereof. The pharmaceutical formulation should be suitable for delivery method. The pharmaceutical composition may be in the form of injections which are made by conventional methods, using physiological saline or other aqueous solution containing glucose or auxiliary substances. The pharmaceutical compositions in the form of tablet or capsule may be prepared by routine methods. The pharmaceutical compositions, e.g., injections, solutions, tablets, and capsules, should be manufactured under sterile conditions. The active ingredient is administrated in therapeutically effective amount, e.g., about 1 ug–5 mg/kg body weight per day. Moreover, the polypeptide of invention can be administrated together with other therapeutic agents.

When using pharmaceutical composition, the safe and effective amount of the Bin1b protein or its antagonist or agonist is administrated to mammals. Typically, the safe and effective amount is at least about 1 ug/kg body weight and less than about 8 mg/kg body weight in most cases, and preferably about 10 ug–1 mg/kg body weight. Certainly, the precise amount depends upon various factors, such as delivery methods, the subject health, etc., and is within the judgment of the skilled clinician.

The polypeptide molecule capable of binding Bin1b protein can be obtained by screening out the random polypeptide library consisting of the various combinations of amino acids bound onto the solid matrix.

The invention further provides diagnostic assays for quantitative and in situ measurement of Bin1b protein level. These assays are known in the art and include FISH assay and radioimmunoassay. The level of Bin1b protein detected in the assay can be used to illustrate the importance of Bin1b protein in diseases and to determine the Bin1b-related diseases.

A method of detecting Bin1b protein in a sample by utilizing the antibody specifically against Bin1b protein comprises the steps of: contacting the sample with the antibody specifically against Bin1b protein; observing the formation of antibody complex which indicates the presence of Bin1b protein in the sample.

The polynucleotide encoding Bin1b protein can be used in the diagnosis and treatment of Bin1b related diseases. In diagnosis, the polynucleotide encoding Bin1b can be used to detect whether Bin1b is expressed or not, and whether the expression is normal or abnormal in the case of diseases. Bin1b DNA sequences can be used in the hybridization with biopsy samples to determine Bin1b expression. The hybridization methods include Southern blotting, Northern blotting and in situ blotting, etc., which are public and sophisticated techniques. The corresponding kits are commercially available. A part of or all of the polynucleotides of the invention can be used as probe and fixed on a microarray or DNA chip for analyzing the differential expression of genes in tissues and for the diagnosis of genes. The Bin1b specific primers can be used in RT-PCR and in vitro amplification to detect the transcripts of Bin1b.

Detection of Bin1b gene mutation is useful for the diagnosis of Bin1b related diseases. The mutation forms of Bin1b include site mutation, translocation, deletion, rearrangement and any other mutations compared with the wild-type Bin1b DNA sequence. The conventional methods, e.g., Southern blotting, DNA sequencing, PCR and in situ blotting, can be used to detect mutation. Moreover, mutation sometimes affects protein expression. Therefore, Northern blotting and Western blotting can be used to indirectly determine the gene mutation.

The sequences of invention are also valuable for chromosome identification. Briefly, sequences can be mapped to chromosomes by preparing PCR primers (preferably 15–35 bp) from the Bin1b cDNA. These primers are then used for PCR screening of somatic cell hybrids containing individual human chromosomes. Only the cell hybrids, which contain the genes corresponding to the primers, produce amplified fragments.

Once a sequence is mapped to a precise chromosomal location, the physical position of the sequence in chromosome can be correlated with genetic map data. Such data are found in, e.g., Mendelian Inheritance in Man (available on-line through Johns Hopkins University Welch Medical Library). The relationships between genes and diseases that have been mapped to the same chromosomal region are then identified through linkage analysis.

The Bin1b provides approach for curing urogenital system diseases and developing male contraception, thus having huge potential applications.

The invention is further illustrated by the following examples. These examples are only intended to illustrate the invention, but not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

EXAMPLE 1

Discovery of Bin1b Differential cDNA Fragment

Mainly following the procedures described by Liang, P. et al. [P. Liang, and A. B. Pardee, Science 257, 967 (1992)], total RNAs were isolated from the caput, corpus and cauda regions of the adult Sprague-Dawley rat epididymis, using RNase-free DNase digestion to remove residual chromosome DNA. After precipitation, retrotranscription was carried out with 2 ug isolated total DNAs and 2.5 uM lower primer $T_{11}$CA with 400 units of MMLV reverse transcriptase (Gibco, BRL) were used. 1/20 of the reverse transcription product was used as template to perform the PCR with 2.5 uM of the upper primer 502 (5'-TGGATTGGTC-3') and 0.5 uM of the lower primer $T_{11}$CA in a 20 ul volume containing 10 mM Tris-HCl pH 9.0, 1.5 mM $MgCl_2$, 50 mM KCl, 0.1% Triton X-100, 4 uM each dNTP, 1 uCi $^{32}$P-dATP and 3 units of Taq polymerase. The PCR conditions were 94° C. for 5 min, then 40 cycles of 94° C. for 30 sec, 40° C. for 60 sec, and 72° C. for 50 sec, with a final elongation at 72° C. for 10 min. PCR products were precipitated and fractionated on the 0.2 mm thick 6% sequencing gel.

The band (~340 bp) differentially displayed only in the RNA from caput region was named Bin1b (FIG. 1) and cut out and left in boiling distilled water for 15 min. The eluted DNAs were precipitated with ethanol and re-amplified in the same conditions as described above except that 40 uM instead of 4 uM each dNTP was used and no radioisotope was involved. The resultant 340 bp DNA fragments were cloned into pBluescript SK (plasmid. 52 clones were screened by reverse Northern and the clone having specific hybridization signal in the caput region was named Bin1b. The full-length cDNA of Bin1b was cloned by 5'-RACE based on said fragment.

EXAMPLE 2

Cloning and Characterization of Full-Length Bin1b cDNA:

Primers were designed based on obtained cDNA fragment for extending the 5' end. Two 5'-RACE approaches were used to obtain full-length cDNA.

The first approach was a conventional method reported by A. N. Apte and P. D. Siebert [in Reverse Transcriptase PCR, J. W. Larrick, P. D. Siebert, Eds. (Horwood, London, 1995), pp. 232-244], using DNA oligo-first strand cDNA ligation.

The other was with DNA oligo —RNA ligation [modified from K, Maruyama, S. Sugano, Gene 138, 171 (1994), to ensure the obtaining of the 5'-capping site]. Oligo DNA was used instead of oligo RNA to ligate with total RNA. The procedure was as follows:

Total RNA (50 ug) from rat epididymis caput was digested with 400 units of bacterial alkaline phosphatase (BAP) at 37° C. for 30 min and additional incubation at 65° C. for 30 min. The BAP was then digested with Proteinase K (50 ng/(1) at 37° C. for 30 min. After purification, 10 ug of RNA was further treated with 2 units of tobacco acid pyrophosphatase (TAP) at 37° C. for 2 hours, extracted with phenol/chloroform, and precipitated with ethanol. The untreated RNA, BAP-treated RNA, and TAP-treated RNA (0.75 ug, about 3 pmol, respectively) were mixed with 1.25 pmol of the DNA oligonucleotide 7209 (5'-AATGGTACCGT-GACGTGGTCC-3') (SEQ ID NO:5) and ligated with T4 RNA ligase (1.2 unit/ul) in 10 ul of 50 mM Tris-HCl (pH 8.0), 10 mM $MgCl_2$, 1 mM hexamine colbalt chloride, 25% PEG 8000, and 1 mM adenosine triphosphate at 17° C. for 18 hours. Superscript II One-Step RT-PCR system (Gibco, BRL) was used to perform the RT-PCR reaction with 0.2 ul of the ligation products in 20 ul containing 200 mM oligo DNA #7209 (5'-AATGGTACCGTGACGTGGTCC-3', SEQ ID NO:5) and 200 mM Bin1b gene-specific primer (GSP) (5'-TGGCCCCGCTGCATGAAGCAC-3', SEQ ID NO:6). The RT-PCR reactions were as follows: 50° C. for 30 min, 94° C. for 2 min, then 35 cycles of 94° C. for 5s, 60° C. for 15s, and 72° C. for 45s, with a final elongation 72° C. for 5 min. The second PCR was performed with 0.2 µl of the RT-PCR products in 10 ul volume containing 50 mM Tris-HCl (pH 8.3), 1–3 mM $MgCl_2$, bovine serum albumin (250 ug/ml), 0.5% Ficoll 400, 1 mM tartrazine, 200 uM dNTP, 500 nM Bin1b GSP 500 nM oligo DNA #7209, and 0.4 unit of Taq polymerase. PCR reactions were run in capillary tubes as follows: 94° C. for 1 min, then 60 cycles of 94° C. for 0s, 60° C. for 0s, and 77° C. for 15s, with a final elongation at 77° C. for 5 min. The PCR product was cloned into pBluescript SK+ T-Vector and sequenced. Thus, the 3' and 5' fragments of Bin1b were obtained.

Primers was designed on both terminals of cDNA fragments (5'-GGACACCCAG TCATCAGTCA-3' (SEQ ID NO:7) and 5'-CAGCAAGTGT TTATTGAGCA-3' (SEQ ID NO:8)). Using RT-PCR product as a template, Bin1b full-length cDNA clone was obtained by PCR. The sequence was confirmed in 6 rats of different ages. Bin1b full-length cDNA was 385 bp (SEQ ID NO:1 and FIG. 2A) which encodes a 68aa peptide (named Bin1b protein) (SEQ ID NO:2) with a signal peptide of 16 amino acids at N-terminal. The putative mature protein contains 45 amino acid (another 7 amino acid was removed during pro-Bin1b maturation).

The result of blast search indicated the coding sequence (180–241) of Bin1b had 83% identity with noncoding sequence (456–518) of human sperm antigen HE2 (673 bp). The peptide coded by Bin1b exhibited some similarity with mammalian beta-defensins. (FIG. 2B) The Bin1b genomic DNA was cloned by similar PCR procedure (SEQ ID NO:4, FIG. 2A). The Bin1b genomic DNA contained two exons separated by an intron, which was characteristic in beta-defensin gene family.

Several isomers of human HE2 and its homologs in chimpanzee, EP2 were reported by several laboratories. Though some of them were low expressed, they shared high sequence homology with Bin1b (FIG. 2C).

EXAMPLE 3

Expression of Bin1b Protein

The size of Bin1b peptide was confirmed to be about 31 kD by in vitro transcription and translation, meeting the theoretical prediction.

Plasmid pSPT18-Bin1b (FIG. 3C) was constructed by cloning Bin1b full-length cDNA (including 75 bp polyA tail) encoding ORF of 68 amino acids (7799 Dalton) between EcoRI and HindIII sites (downstream of T7 promoter) of pSPT18 (Promega). The plasmid was completely digested by HindIII. The reaction was performed with TNT T7 Coupled Reticulocyte Lysate System labeled by $^{35}$S-Met and then analyzed by 16.5% Tricine-SDS-PAGE as described by Schagger and Von Jagow. The result was shown in FIG. 3A. The result was compared with negative control without plasmid DNA and luciferase SP6 and T7 (FIG. 3B).

EXAMPLE 4

Fusion Expression of Bin1b and Antibody Preparation

A fragment of Bin1b cDNA (126–281) was cloned into fusion expression vector pQE-40 (QIAGEN). The positive clone was induced with 1 mM IPTG and purified by Ni-NTA agarose (Qiagen) as described by the manufacturer (see QiaExpressionist, Qiagen).

The purified fusion protein DHFR-Bin1b is 31 KD (FIG. 4). Rabbit was immunized with the purified protein to produce the antiserum to DHFR-1b. But the titer of the antiserum to Bin1b was still to be improved.

EXAMPLE 5

Tissue distribution of Bin1b

Tissue distribution analysis of Bin1b was done by Northern blot following the method of Church and Gilbert (1984). Total RNA was extracted from epididymis caput, testis, ventral prostate, liver, heart, spleen, lung, kidney, thymus, adrenal gland, coagulating gland, seminal vesicle, hypothalamus, striatum, pituitary, hippocampus, cerebellum, cerebral cortex and epididymis caput of Sprague-Dawley rat, respectively. 20 ug each of total RNA was separated on 1.2% formaldehyde agarose gel electrophoresis and transferred to Hybond-N+ membrane (Amersham Pharmacia Biotech). Bin1b probe was labeled by Prime-a-Gene (System kit (Promega). The result of hybridization indicated that Bin1b was only expressed on rat caput epididymis (FIG. 5A). In situ hybridization was used to decide the precise localization of Bin1b in epididymis.

EXAMPLE 6

Localization of Bin1b mRNA in Epididymis

In this example, conventional in situ hybridization was used to map Bin1b. Microscopy showed that Bin1b was localized to the epithelial of middle caput epididymis. (FIGS. 5B-E)

EXAMPLE 7

Developmental Change of Bin1b During Rat Growth

Developmental change of Bin1b was analyzed by in the same northern blot as in Example 5. RNA was extracted from caput epididymis of 15 day-old rat; caput, corpus and cauda epididymis of 30, 45, 60, 120, 270 and 720 day-old rat.

Figure 5F:
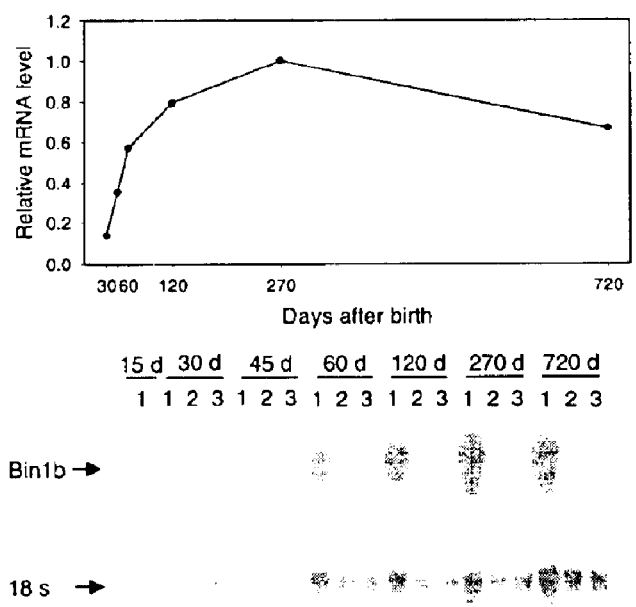
FIG. 5F. The expression profile of Bin1b mRNA in the rat epididymis during the whole life span (15–720 days). (1, 2 and 3 represent the mRNA from the caput, corpus and cauda regions, respectively)

The result showed that expression of Bin1b was highest at sexually mature period (including sexually active period) and gradually decrease afterwards (FIG. 5F). This indicated that Bin1b might be associated with sperm maturation and regulate Bin1b for male contraception.

EXAMPLE 8

Bin1b expression is regulated by small moleculars such as hormones.

In this example, the study on EDS rat model showed that Bin1b expression was partially up-regulated by androgen. Adult Sprague-Dawley was intraperitoneally injected with EDS (7.5 mg/100 g bodyweight) in $DMSO-H_2O$ (1:3, v/v). The rats were sacrificed on day 1, 3, 7, 14, 21, 28 and 42. The rat without EDS injection served as the negative control. 20 ug total RNA was extracted from rat caput epididymis, fractionated by 1.2% formaldehyde agarose gel electrophoresis, blotted onto Hybond-N+ membrane and hybridized with a probe located at Bin1b cDNA 3' terminal and 18s ribosome RNA probe.

Figure 6A:
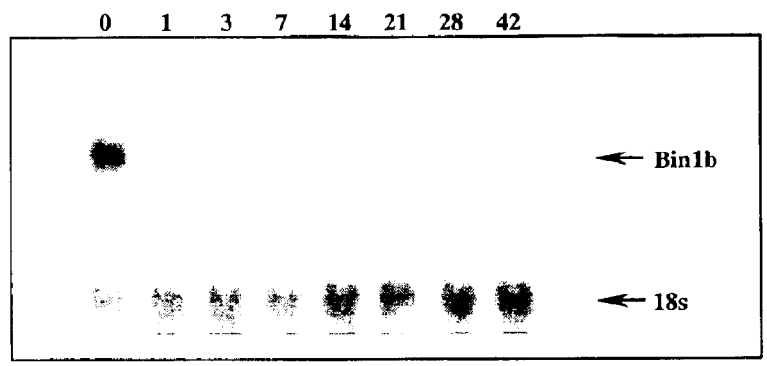
FIG. 6A. Northern blot analysis picture.
Figure 6B:
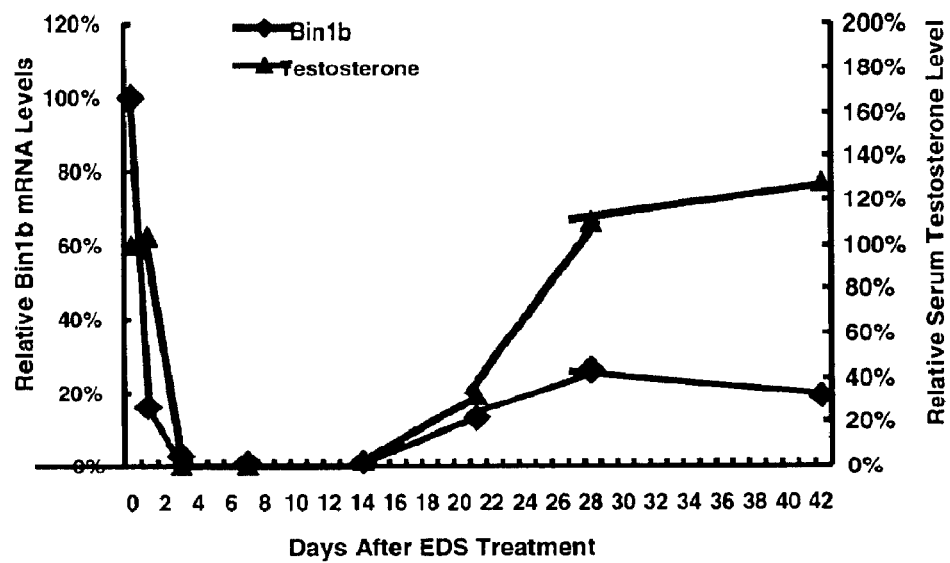
FIG. 6B shows Bin1b expression is up-regulated by androgen. The "▲" line represents rat serum testosterone level at various time intervals after EDS injection. The "♦" line represents rat Bin1b expression changes which are calibrated by 18s level.

The secretion of androgen decreased immediately after EDS injection but restored in about two weeks after injection. The expression of Bin1b was up-regulated by androgen compared with variation of androgen level (FIGS. 6A and 6B).

It is possible to control sperm maturation by regulation of Bin1b expression with small hormone molecule, which pave new way for developing male contraceptives.

EXAMPLE 9

Bin1b is a Native Antimicrobial Peptide

The studies above indicated Bin1b was a member of beta-defensin gene family and involved in sperm maturation. The antimicrobial activity was confirmed in this Example.

Figure 7A:
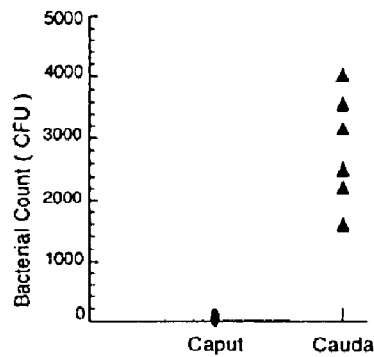
FIG. 7A. Comparison of antimicrobial activity in caput and cauda cultures. 100 colony forming units (CFU) of $E.$ $coli$ was added to cultures 16 hours prior to examination.

The antimicrobial activity of Bin1b was tested with the secretions of primary cultures of caput epididymal epithelial. A total of 100 colony-forming units (CFU) of *E. coli* was added to the apical compartment of the epithelial cells separately from caput epididymis and cauda epididymis. The medium was collected 16 hours later for CFU counting. Strong bactericidal activity was detected in the medium collected from caput culture, but none in cauda culture, which confirmed that secretion from caput epididymis cell had the antimicrobial activity (FIG. 7A).

Figure 7B:
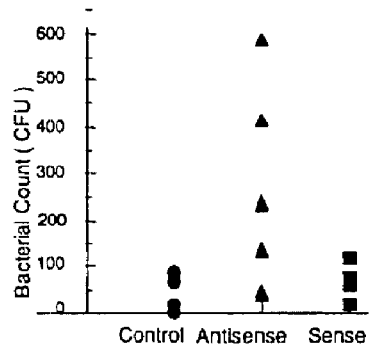
FIG. 7B. Effect of antisense of Bin1b on antimicrobial activity of the caput cultures. The cultures were transfected with antisense or sense oligos (5 ug/l) for 20 hours.

To confirm that the antimicrobial activity was indeed contributed by Bin1b although it was expressed in the caput epididymis, the inventors designed antisense RNAs of Bin1b and added them into cultures to block Bin1b expression 24 hours before adding *E. coli*. The antibacterial capability of the caput culture was greatly attenuated, proving the antimicrobial activity of Bin1b. (FIG. 7B)

These results indicate that Bin1b was a novel native antimicrobial peptide in beta-defensin family.

EXAMPLE 10

Bin1b Expression was Up-Regulated by Inflammation

Figure 7C:
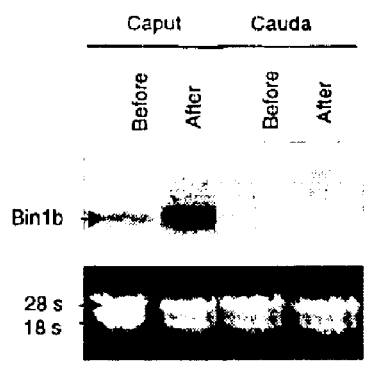
FIG. 7C. Enhanced Bin1b mRNA in the caput but not the cauda region of the rat epididymis inflamed by two-week ligation of the spermaductus.

When inflammation resulted from ligation of spermaductus which led to accumulation of sperm in epididymis occurred, Bin1b mRNA in caput epididymis increased to 3 folds of normal level before the ligation. No change was seen in cauda epididymis (FIG. 7C). This indicated that Bin1b expression was up-regulated by inflammation.

All the documents cited herein are incorporated into the invention as reference, as if each of them is individually incorporated. Further, it would be appreciated that, in the above teaching of invention, the skilled in the art could make certain changes or modifications to the invention, and these equivalents would still be within the scope of the invention defined by the appended claims of the application.

---

What is claimed is:

1. An isolated polypeptide comprising the amino acid sequence of SEQ ID NOs: 2 or 3.

2. The polypeptide of claim 1 wherein the sequence of the polypeptide is SEQ ID NOs: 2 or 3.

3. A pharmaceutical composition comprising a pharmaceutically acceptable carrier and from about 1 ug to about 5 mg/kg body weight per day of the polypeptide of claim 1.

4. A microbicide comprising an effective amount of the polypeptide of claim 1.

5. The polypeptide of claim 1 which is encoded by a polynucleotide selected from the group consisting of (a) 57–260 of SEQ ID NO: 1; (b) 105–260 of SEQ ID NO:1; and (c) 1–336 of SEQ ID NO:1.

* * * * *